US012414912B2

(12) United States Patent
Anapolle

(10) Patent No.: US 12,414,912 B2
(45) Date of Patent: Sep. 16, 2025

(54) TOPICAL PRODUCT INCLUDING APPLE

(71) Applicant: Ross Anapolle, Newton, MA (US)

(72) Inventor: Ross Anapolle, Newton, MA (US)

( * ) Notice: Subject to any disclaimer, the term of this patent is extended or adjusted under 35 U.S.C. 154(b) by 357 days.

(21) Appl. No.: 17/741,999

(22) Filed: May 11, 2022

(65) Prior Publication Data
US 2023/0034385 A1 Feb. 2, 2023

Related U.S. Application Data

(63) Continuation-in-part of application No. 15/693,897, filed on Sep. 1, 2017, now abandoned.

(60) Provisional application No. 62/382,375, filed on Sep. 1, 2016, provisional application No. 62/382,399, filed on Sep. 1, 2016.

(51) Int. Cl.
*A61K 36/00* (2006.01)
*A61K 8/9789* (2017.01)

(52) U.S. Cl.
CPC ........ *A61K 8/9789* (2017.08); *A61K 2800/10* (2013.01)

(58) Field of Classification Search
CPC ............................ A61K 2800/10; A61Q 19/00
See application file for complete search history.

(56) References Cited

U.S. PATENT DOCUMENTS

| | | | |
|---|---|---|---|
| 1,333,967 | A | 3/1920 | Fowler, Jr. et al. |
| 4,971,823 | A | 11/1990 | Fahlen |
| 5,534,280 | A | 7/1996 | Welch |
| 8,551,554 | B2 | 10/2013 | Liu |
| 10,893,693 | B1 | 1/2021 | Anapolle |
| 2002/0187219 | A1 | 12/2002 | Yang et al. |
| 2004/0265451 | A1 | 12/2004 | Rooks et al. |
| 2005/0069616 | A1 | 3/2005 | Lee et al. |
| 2005/0147723 | A1* | 7/2005 | Liu ................... A23L 19/01 426/489 |
| 2007/0003680 | A1 | 1/2007 | Tachdjian |
| 2007/0014914 | A1 | 1/2007 | Borders et al. |
| 2009/0110789 | A1 | 4/2009 | Mower et al. |
| 2011/0152371 | A1 | 6/2011 | Rupasinghe et al. |
| 2018/0055761 | A1 | 3/2018 | Anapolle |
| 2019/0357580 | A1 | 11/2019 | Levy |
| 2021/0195929 | A1 | 7/2021 | Nowak et al. |
| 2023/0034385 | A1 | 2/2023 | Anapolle |
| 2024/0324642 | A1 | 10/2024 | Anapolle |

FOREIGN PATENT DOCUMENTS

| | | | |
|---|---|---|---|
| CN | 104083301 | A * | 10/2014 |
| CN | 104622757 | | 5/2015 |
| CN | 105613871 | A | 6/2016 |
| JP | 2002275026 | | 9/2002 |
| WO | WO 2006/068512 | A1 | 6/2006 |
| WO | 2007026101 | | 3/2007 |

OTHER PUBLICATIONS

Andujar, Recio, et al, "Cocoa Polyphenols and Their Potential Benefits for Human Health". Oxidative Medicine and Cellular Longevity, 2012, 23 pages, vol. 2012, Article ID 960252, Hindawi Publishing Corporation.
Anunciato, Talita P.,et al, "Carotenoids and Polyphenols in Nutricosmetics, Nutraceuticals, and Cosmeceuticals". Journal of Cosmetic Dermatology, 2012, pp. 51-54, 11, 2012 Wiley Periodicals.
Chen, Jian, et al, "Inhibitory Mechanism and Kinetics Study of Apple Polyphenols on the Activity of Tyrosinase". International Journal of Food Properties, 2014, pp. 1694-1701, vol. 17:8, Published online http://dx.doi.org/10.1080/10942912.2012.675606.
Epstein, Howard, Cosmeceuticals and Polyphenols, Clinics in Dermatology, 2009, pp. 475-478, 27.
Gennaro, A (Ed.). "Remington's Pharmaceutical Science 17th Edition". (1985) pp. 1492, 1513, 1516-1517.
Lee, J. and Mitchell, A, "Pharmacokinetics of Quercetin Absorption from Apples and Onions in Healthy Humans". Journal of Agricultural and Food Chemistry, 2012, pp. 3874-3881, 60.
Nadium, M., et al, "Improvement of Polyphenol upon Glucosylation in a UV-induced skin cell ageing model". International Journal of Cosmetic Science, 2014, pp. 579-587, 36.
Palermo et al. "Apple Can Act As Anti-Aging on Yeast Cells", Oxidative Medicine and Cellular Longevity, vol. 2012, Article ID 491759, 8 pages. (2012).
Ratz-Lyko, Anna, et al, "Influence of Polyphenols on the Physiological Processes in the Skin". Phyotheraphy Research, 2015, pp. 509-517, vol. 29, Published online Jan. 14, 2015 in Wiley Online Library www.wileyonlinelibrary.com.
Virk, B.S., et al, "Extraction and Characterization of Pectin from Apple (Malus Pumila. Cv Amri) Peel Waste". International Journal of Food Properties, pp. 693-703, 2004, Marcel Dekker, Inc. New York, NY, http://www.tandfonline.com/doi/abs/10.1081/JFP-200033095.
Warren, RM. "10 Smoothie Recipes For Younger Looking Skin", Prevention.com. Internet posting date: Jun. 11, 2015. Retrieved from the Internet on Dec. 17, 2020 from URL: https:// www.prevention.com/beauty/a20463851 /smoothie-recipes-for-skin/. (2015).
International Search Report and Written Opinion for International Application No. PCT/US2024/021478 dated Jun. 17, 2024.
International Search Report and Written Opinion for International Application No. PCT/US2024/044541 dated Nov. 4, 2024.
[No Author Listed], How to Dry Apples. Jennifers Kitchen. Dec. 2011. https://jenniferskitchen.com/2011/12/how-to-dry-apples.html [last accessed Aug. 20, 2024]: 1 page.

(Continued)

*Primary Examiner* — Qiuwen Mi
(74) *Attorney, Agent, or Firm* — Wolf, Greenfield & Sacks, P.C.

(57) ABSTRACT

Provided is a topical apple product, comprising a base topical product configured for application to a human and an apple material substantially uniformly combined with the base topical material. Also provided is a method of treating a skin condition or ailment with topical apple product. The apple material can have a Polyphenols/Total Antioxidant Activity of ≥3.00%.

21 Claims, 3 Drawing Sheets

(56) References Cited

OTHER PUBLICATIONS

Aprea et al., Sweet taste in apple: the role of sorbitol, individual sugars, organic acids and volatile compounds. Sci Rep. Mar. 21, 2017;7:44950. doi: 10.1038/srep44950.
Augustin et al., Dietary glycemic index and glycemic load, and breast cancer risk: a case-control study. Ann Oncol. Nov. 2001;12(11):1533-8. doi: 10.1023/a:1013176129380.
Boyer et al., Apple phytochemicals and their health benefits. Nutr J. May 12, 2004;3:5. doi: 10.1186/1475-2891-3-5.
Boyer et al., In vitro digestion and lactase treatment influence uptake of quercetin and quercetin glucoside by the Caco-2 cell monolayer. Nutr J. Jan. 11, 2005;4:1. doi: 10.1186/1475-2891-4-1.
Boyer et al., Uptake of quercetin and quercetin 3-glucoside from whole onion and apple peel extracts by Caco-2 cell monolayers. J Agric Food Chem. Nov. 17, 2004;52(23):7172-9. doi: 10.1021/jf030733d.
Brand et al., Food processing and the glycemic index. Am J Clin Nutr. Dec. 1985;42(6):1192-6. doi: 10.1093/ajcn/42.6.1192.
Broadbent et al., Oil stability index correlated with sensory determination of oxidative stability in canola oil. J Am Oil Chem Soc. Jan. 2003;80(1):59-63.
Brouns et al., Glycaemic index methodology. Nutr Res Rev. Jun. 2005;18(1):145-71. doi: 10.1079/NRR2005100.
Carson et al., Unrefined, Dried Apple Pomace as a Potential Food Ingredient. J Food Sci. Nov. 1994;59(6):1213-5.
Chen et al., Modulation of gut microbiota by mulberry fruit polysaccharide treatment of obese diabetic db/db mice. Food Funct. Jul. 17, 2018;9(7):3732-3742. doi: 10.1039/c7fo01346a.
Chen et al., Potential Mechanisms of Action of Dietary Phytochemicals for Cancer Prevention by Targeting Cellular Signaling Transduction Pathways. J Agric Food Chem. Apr. 4, 2018;66(13):3260-3276. doi: 10.1021/acs.jafc.7b04975. Epub Mar. 21, 2018.
Chu et al., Antioxidant and antiproliferative activities of common vegetables. J Agric Food Chem. Nov. 6, 2002;50(23):6910-6. doi: 10.1021/jf020665f.
Chu et al., Novel low-density lipoprotein (LDL) oxidation model: antioxidant capacity for the inhibition of LDL oxidation. J Agric Food Chem. Nov. 3, 2004;52(22):6818-23. doi: 10.1021/jf040099j.
Ebbeling et al., A reduced-glycemic load diet in the treatment of adolescent obesity. Arch Pediatr Adolesc Med. Aug. 2003;157(8):773-9. doi: 10.1001/archpedi.157.8.773.
Eberhardt et al., Antioxidant activity of fresh apples. Nature. Jun. 22, 2000;405(6789):903-4. doi: 10.1038/35016151.
Franceschi et al., Dietary glycemic load and colorectal cancer risk. Ann Oncol. Feb. 2001;12(2):173-8. doi: 10.1023/a:1008304128577.
Gao et al., A full utilization of rice husk to evaluate phytochemical bioactivities and prepare cellulose nanocrystals. Sci Rep. Jul. 11, 2018;8(1):10482. doi: 10.1038/s41598-018-27635-3.
He et al., Changes in polyphenol fractions and bacterial composition after in vitro fermentation of apple peel polyphenol by gut microbiota. Int J Food Sci Technol. Jul. 2022;57(7):4268-76. doi: 10.1111/ijfs.15751.
He et al., Phytochemicals of apple peels: isolation, structure elucidation, and their antiproliferative and antioxidant activities. J Agric Food Chem. Nov. 12, 2008;56(21):9905-10. doi: 10.1021/jf8015255. Epub Oct. 2, 2008.
He et al., Triterpenoids isolated from apple peels have potent antiproliferative activity and may be partially responsible for apple's anticancer activity. J Agric Food Chem. May 30, 2007;55(11):4366-70. doi: 10.1021/jf0635630. Epub May 8, 2007.
Ibarz et al., Rheological behaviour of apple juice and pear juice and their concentrates. J Food Eng. 1987;6(4):257-67.
Jebe et al., Collaborative study of the oil stability index analysis. J Am Oil Chem Soc. Nov. 1993;70(11):1055-61.
Jenkins et al., Glycemic index of foods: a physiological basis for carbohydrate exchange. Am J Clin Nutr. Mar. 1981;34(3):362-6. doi: 10.1093/ajcn/34.3.362.
Jiang et al., 2α-Hydroxyursolic Acid Inhibited Cell Proliferation and Induced Apoptosis in MDA-MB-231 Human Breast Cancer Cells through the p38/MAPK Signal Transduction Pathway. J Agric Food Chem. Mar. 2, 2016;64(8):1806-16. doi: 10.1021/acs.jafc.5b04852. Epub Feb. 19, 2016.
Larsen et al., Diets with high or low protein content and glycemic index for weight-loss maintenance. N Engl J Med. Nov. 25, 2010;363(22):2102-13. doi: 10.1056/NEJMoa1007137.
Li et al., Bioactive compounds of highland barley and their health benefits. J Cereal Sci. Jan. 2022;103:103366. doi: 10.1016/j.jcs.2021.103366.
Li et al., Ferulic Acid Mediates Metabolic Syndrome via the Regulation of Hepatic Glucose and Lipid Metabolisms and the Insulin/IGF-1 Receptor/PI3K/AKT Pathway in Palmitate-Treated HepG2 Cells. J Agric Food Chem. Nov. 23, 2022;70(46):14706-14717. doi: 10.1021/acs.jafc.2c05676. Epub Nov. 11, 2022.
Liu et al., A prospective study of dietary fiber intake and risk of cardiovascular disease among women. J Am Coll Cardiol. Jan. 2, 2002;39(1):49-56. doi: 10.1016/s0735-1097(01)01695-3.
Liu et al., Antioxidants and Whole Food Phytochemicals for Cancer Prevention. In: Antioxidant Measurement and Applications. Shahidi et al., Eds. Mar. 2007;Chapter 3:15-34.
Liu et al., Antiproliferative activity of apples is not due to phenolic-induced hydrogen peroxide formation. J Agric Food Chem. Mar. 12, 2003;51(6):1718-23. doi: 10.1021/jf026162r.
Liu et al., Apples prevent mammary tumors in rats. J Agric Food Chem. Mar. 23, 2005;53(6):2341-3. doi: 10.1021/jf058010c.
Liu et al., Fresh apples suppress mammary carcinogenesis and proliferative activity and induce apoptosis in mammary tumors of the Sprague-Dawley rat. J Agric Food Chem. Jan. 14, 2009;57(1):297-304. doi: 10.1021/jf801826w.
Liu et al., Potential cell culture models for antioxidant research. J Agric Food Chem. May 18, 2005;53(10):4311-4. doi: 10.1021/jf058070i.
Liu, Dietary bioactive compounds and their health implications. J Food Sci. Jun. 2013;78 Suppl 1:A18-25. doi: 10.1111/1750-3841.12101.
Liu, Health benefits of fruit and vegetables are from additive and synergistic combinations of phytochemicals. Am J Clin Nutr. Sep. 2003;78(3 Suppl):517S-520S. doi: 10.1093/ajcn/78.3.517S.
Liu, Health-promoting components of fruits and vegetables in the diet. Adv Nutr. May 1, 2013;4(3):384S-92S. doi: 10.3945/an.112.003517.
Liu, Potential synergy of phytochemicals in cancer prevention: mechanism of action. J Nutr. Dec. 2004;134(12 Suppl):3479S-3485S. doi: 10.1093/jn/134.12.3479S.
Liu, Protective role of phytochemicals in whole foods: Implications for chronic disease prevention. Appl Biotechnol Food Sci Policy. 2003;1(1):39-46.
Pang et al., Averrhoa carambola free phenolic extract ameliorates nonalcoholic hepatic steatosis by modulating mircoRNA-34a, mircoRNA-33 and AMPK pathways in leptin receptor-deficient db/db mice. Food Funct. Dec. 13, 2017;8(12):4496-4507. doi: 10.1039/c7fo00833c.
Rupasinghe et al., Effect of baking on dietary fibre and phenolics of muffins incorporated with apple skin powder. Food Chem. Apr. 1, 2008;107(3):1217-24.
Sair et al., Anticancer activity of apple peel extracts against human breast cancer cells through insulin-like growth factor-1 signal transduction pathway. J Agric Food Res. Mar. 2023; 11:100507.
Sair et al., Molecular regulation of phenolic compounds on IGF-1 signaling cascade in breast cancer. Food Funct. Mar. 21, 2022;13(6):3170-3184. doi: 10.1039/d1fo03283f.
Salmeron et al., Dietary fiber, glycemic load, and risk of NIDDM in men. Diabetes Care. Apr. 1997;20(4):545-50. doi: 10.2337/diacare.20.4.545.
Salmeron et al., Dietary fiber, glycemic load, and risk of non-insulin-dependent diabetes mellitus in women. JAMA. Feb. 12, 1997;277(6):472-7. doi: 10.1001/jama.1997.03540300040031.
Song et al., Cellular antioxidant activity of common vegetables. J Agric Food Chem. Jun. 9, 2010;58(11):6621-9. doi: 10.1021/jf9035832.

(56) References Cited

OTHER PUBLICATIONS

Song et al., Combination of apple peel and blueberry extracts synergistically induced lifespan extension via DAF-16 in Caenorhabditis elegans. Food Funct. Jul. 22, 2020;11(7):6170-6185. doi: 10.1039/d0fo00718h.

Song et al., Mitochondria are involved in the combination of blueberry and apple peel extracts synergistically ameliorating the lifespan and oxidative stress in Caenorhabditis elegans. Food Funct. Aug. 1, 2022;13(15):8204-8213. doi: 10.1039/d2fo00474g.

Song et al., SKN-1 is involved in combination of apple peels and blueberry extracts synergistically protecting against oxidative stress in Caenorhabditis elegans. Food Funct. Jun. 24, 2020;11(6):5409-5419. doi: 10.1039/d0fo00891e.

Sun et al., Antioxidant and antiproliferative activities of common fruits. J Agric Food Chem. Dec. 4, 2002;50(25):7449-54. doi: 10.1021/jf0207530.

Sun et al., Apple phytochemical extracts inhibit proliferation of estrogen-dependent and estrogen-independent human breast cancer cells through cell cycle modulation. J Agric Food Chem. Dec. 24, 2008;56(24):11661-7. doi: 10.1021/jf8021223.

Van Dam et al., Dietary glycemic index in relation to metabolic risk factors and incidence of coronary heart disease: the Zutphen Elderly Study. Eur J Clin Nutr. Sep. 2000;54(9):726-31. doi: 10.1038/sj.ejcn.1601086.

Vayndorf et al., Whole apple extracts increase lifespan, healthspan and resistance to stress in Caenorhabditis elegans. J Funct Foods. Jul. 2013;5(3):1236-1243. doi: 10.1016/j.jff.2013.04.006.

Venugopal et al., Phytochemicals in diets for breast cancer prevention: The importance of resveratrol and ursolic acid. Food Sci Human Wellness. Dec. 2012;1(1):1-13.

Wang et al., Blueberry extract promotes longevity and stress tolerance via DAF-16 in Caenorhabditis elegans. Food Funct. Oct. 17, 2018;9(10):5273-5282. doi: 10.1039/c8fo01680a.

Wang et al., Comparative suppression of NLRP3 inflammasome activation with LPS-induced inflammation by blueberry extracts (*Vaccinium* spp.). RSC Adv. Jun. 2017;7(46):28931-9.

Wang et al., Comparison of phytochemical profiles, antioxidant and cellular antioxidant activities of different varieties of blueberry (*Vaccinium* spp.). Food Chem. Feb. 15, 2017;217:773-781. doi: 10.1016/j.foodchem.2016.09.002. Epub Sep. 3, 2016.

Wang et al., Mechanisms underlying the protective effects of blueberry extract against ultraviolet radiation in a skin cell co-culture system. J Func Foods. Jan. 2019;52:603-10.

Wen et al., Phytochemical profiles and cellular antioxidant activity of Malus doumeri (bois) chevalier on 2,2'-azobis (2-amidinopropane) dihydrochloride (ABAP)-induced oxidative stress. J Func Foods. Aug. 2016;25:242-56.

Wolever et al., Determination of the glycaemic index of foods: interlaboratory study. Eur J Clin Nutr. Mar. 2003;57(3):475-82. doi: 10.1038/sj.ejcn.1601551.

Wolever et al., Measuring the glycemic index of foods: interlaboratory study. Am J Clin Nutr. Jan. 2008;87(1):247S-257S. doi: 10.1093/ajcn/87.1.247S.

Wolever et al., The glycemic index: methodology and clinical implications. Am J Clin Nutr. Nov. 1991;54(5):846-54. doi: 10.1093/ajcn/54.5.846.

Wolfe et al., Antioxidant activity of apple peels. J Agric Food Chem. Jan. 29, 2003;51(3):609-14. doi: 10.1021/jf020782a.

Wolfe et al., Apple peels as a value-added food ingredient. J Agric Food Chem. Mar. 12, 2003;51(6):1676-83. doi: 10.1021/jf025916z.

Wolfe et al., Cellular antioxidant activity (CAA) assay for assessing antioxidants, foods, and dietary supplements. J Agric Food Chem. Oct. 31, 2007;55(22):8896-907. doi: 10.1021/jf0715166. Epub Sep. 29, 2007.

Wolfe et al., Cellular antioxidant activity of common fruits. J Agric Food Chem. Sep. 24, 2008;56(18):8418-26. doi: 10.1021/jf801381y. Epub Aug. 30, 2008.

Wolfe et al., Structure-activity relationships of flavonoids in the cellular antioxidant activity assay. J Agric Food Chem. Sep. 24, 2008;56(18):8404-11. doi: 10.1021/jf8013074. Epub Aug. 15, 2008.

Xi et al., Whole food approach for type 2 diabetes prevention. Mol Nutr Food Res. Aug. 2016;60(8):1819-36. doi: 10.1002/mnfr.201500963. Epub Jun. 14, 2016.

Xing et al., Investigation into the mechanisms of quercetin-3-O-glucuronide inhibiting α-glucosidase activity and non-enzymatic glycation by spectroscopy and molecular docking. Food Funct. Sep. 7, 2021;12(17):7825-7835. doi: 10.1039/d1fo01042e. Epub Jul. 7, 2021.

Xiong et al., Goji berry (*Lycium* spp.) extracts exhibit antiproliferative activity via modulating cell cycle arrest, cell apoptosis, and the p53 signaling pathway. Food Funct. Jul. 20, 2021;12(14):6513-6525. doi: 10.1039/d1fo01105g.

Xiong et al., HSF-1 and SIR-2.1 linked insulin-like signaling is involved in goji berry (*Lycium* spp.) extracts promoting lifespan extension of Caenorhabditis elegans. Food Funct. Sep. 7, 2021;12(17):7851-7866. doi: 10.1039/d0fo03300f. Epub Jul. 9, 2021.

Xu et al., Ovalbumin as an Outstanding Pickering Nanostabilizer for High Internal Phase Emulsions. J Agric Food Chem. Aug. 22, 2018;66(33):8795-8804. doi: 10.1021/acs.jafc.8b02183. Epub Aug. 9, 2018.

Yang et al., DAF-16 is involved in colonic metabolites of ferulic acid-promoted longevity and stress resistance of Caenorhabditis elegans. J Sci Food Agric. Dec. 2022;102(15):7017-7029. doi: 10.1002/jsfa.12063. Epub Jun. 29, 2022.

Yang et al., Nobiletin Delays Aging and Enhances Stress Resistance of Caenorhabditis elegans. Int J Mol Sci. Jan. 4, 2020;21(1):341. doi: 10.3390/ijms21010341.

Yang et al., Synergistic effect of apple extracts and quercetin 3-beta-d-glucoside combination on antiproliferative activity in MCF-7 human breast cancer cells in vitro. J Agric Food Chem. Sep. 23, 2009;57(18):8581-6. doi: 10.1021/jf8039796.

Yin et al., Ursolic acid, a potential anticancer compound for breast cancer therapy. Crit Rev Food Sci Nutr. Mar. 4, 2018;58(4):568-574. doi: 10.1080/10408398.2016.1203755. Epub Oct. 4, 2017.

Yoon et al., Effect of 2alpha-hydroxyursolic acid on NF-kappaB activation induced by TNF-alpha in human breast cancer MCF-7 cells. J Agric Food Chem. Sep. 24, 2008;56(18):8412-7. doi: 10.1021/jf8012844. Epub Aug. 14, 2008.

Yoon et al., Effect of selected phytochemicals and apple extracts on NF-kappaB activation in human breast cancer MCF-7 cells. J Agric Food Chem. Apr. 18, 2007;55(8):3167-73. doi: 10.1021/jf0632379. Epub Mar. 21, 2007.

Zhang et al., Antiproliferative Activity of Ursolic Acid in MDA-MB-231 Human Breast Cancer Cells through Nrf2 Pathway Regulation. J Agric Food Chem. Jul. 15, 2020;68(28):7404-7415. doi: 10.1021/acs.jafc.0c03202. Epub Jul. 2, 2020.

Zhang et al., Lactobacillus salivarius REN inhibits rat oral cancer induced by 4-nitroquioline 1-oxide. Cancer Prev Res (Phila). Jul. 2013;6(7):686-94. doi: 10.1158/1940-6207.CAPR-12-0427. Epub May 8, 2013.

Zhao et al., The Transcription Factor DAF-16 is Essential for Increased Longevity in C. elegans Exposed to Bifidobacterium longum BB68. Sci Rep. Aug. 7, 2017;7(1):7408. doi: 10.1038/s41598-017-07974-3.

\* cited by examiner

TOPICAL PRODUCT INCLUDING APPLE

CROSS REFERENCE TO RELATED APPLICATIONS

The present application is a continuation of U.S. application Ser. No. 15/693,897 filed Sep. 1, 2017, entitled TOPICAL PRODUCT INCLUDING APPLE, which claimed priority under 35 USC 119(e) from provisional application Ser. No. 62/382,375, entitled TOPICAL PRODUCT INCLUDING DRIED APPLE PEEL POWDER, filed on Sep. 1, 2016, and provisional application Ser. No. 62/382,399, entitled TOPICAL PRODUCT INCLUDING APPLE PEEL EXTRACT, filed on Sep. 1, 2016, which are incorporated herein by reference in their entireties.

FIELD OF INTEREST

The present inventive concepts relate to the field of topical products, in particular, the present invention relates to topical products comprising apple, apple constituents, and/or apple byproducts, such as apple peel powder, apple extract, and the like.

SUMMARY

In accordance with aspects of the present disclosure, provided is a topical product comprising an apple material, sometimes referred to herein as a "topical apple product." The apple material can take the form of an apple peel powder, liquid extract, or the like. The apple material can comprise apple peel, apple, flesh and/or combinations thereof. The topical apple product can comprise the apple material combined with a base topical product. The topical apple product can take the form of a liquid, lotion, gel, paste, salve, ointment, cream, rub, powder, extract, wax, or spray, as examples, that can be applied to skin, hair, teeth, and/or nails.

In accordance with aspects of the present disclosure, provided is a topical product, comprising a base topical product configured for application to a human and an apple material substantially uniformly combined with the base topical material.

In various embodiments, the apple material comprises dried apple peel powder.

In various embodiments, the apple material comprises liquid apple extract.

In various embodiments, the apple material comprises apple peel.

In various embodiments, the apple material comprises apple flesh.

In various embodiments, the apple material comprises antioxidants.

In various embodiments, the apple material comprises Polyphenols/Total Antioxidant Activity of ≥3.00%.

In various embodiments, the apple peel extract comprises Polyphenols/Total Antioxidant Activity in a range of about 20% to about 35%.

In various embodiments, the base topical product is a cosmetic product.

In various embodiments, the cosmetic product is chosen from a group consisting of: face and/or body lotion, such as moisturizers and cleansers, skin serums, body powder, sunscreen, bronzer, shampoo, conditioner, soap, hair color, hair detangler, mask, peel, lipstick, lip gloss, lip balm, foundation, blush, toner, mascara, eye shadow, eye and/or anti-aging solutions, shave cream, lotion, or gel, aftershave, deodorant, antiperspirant, cologne, perfume, body splash, toothpaste, floss, and/or mouthwash and/or mouth rinse.

In various embodiments, the base topical material is chosen from a group consisting of: medical treatment product, such as a first aid cream or spray or other skin treatment cream or spray, such as for use to treat a wound, skin irritation, burn, rash, eczema, infection, and/or melanoma, or the like.

In various embodiments, the topical apple product is suitable for application to human skin.

In various embodiments, the topical apple product is suitable for application to human hair.

In various embodiments, the topical apple product is suitable for application to human teeth.

In various embodiments, a percentage of apple material in the topical apple product is greater than 0% and up to about 50%.

In various embodiments, the percentage of apple material in the topical apple product is greater than 0% and up to about 25%.

In various embodiments, the percentage of apple material in the topical apple product is greater than 0% and up to about 10%.

In accordance with another aspect of the inventive concept, provided is a topical applicant product, comprising a base topical product configured for application to a human and an apple material substantially uniformly combined with the base topical material. The apple material is a dried apple peel powder having Polyphenols/Total Antioxidant Activity of ≥3.00%, the apple peel extract topical is suitable for application to human skin, and the base topical product is chosen from a group consisting of: face and/or body lotion, such as moisturizers and cleansers, skin serums, body powder, sunscreen, bronzer, shampoo, conditioner, soap, hair color, hair detangler, mask, peel, lipstick, lip gloss, lip balm, foundation, blush, toner, mascara, eye shadow, eye and/or anti-aging solutions, shave cream, lotion, or gel, aftershave, deodorant, antiperspirant, cologne, perfume, body splash, toothpaste, floss, and/or mouthwash and/or mouth rinse.

In accordance with another aspect of the inventive concept, provided is a method of treating a skin condition and/or ailment, including applying a topical apple product to a portion of skin condition repair skin dryness, irritation, rash, and/or melanoma.

In various embodiment, the apple material has a Polyphenols/Total Antioxidant Activity of ≥3.00%.

In accordance with aspects of the present disclosure, provided is a method of making a topical apple product, comprising providing a base topical product configured for application to a human and combining an apple material with the topical product.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings:

FIG. 1 is a front view of a container partially filled with a base topical product, in accordance with the prior art;

FIG. 2 is a front view of an embodiment of a container partially filled with an apple material, in accordance with aspects of the inventive concept;

FIG. 3 is a notional view of an embodiment of a process for making a topical apple product, in accordance with aspects of the inventive concept;

DETAILED DESCRIPTION OF PREFERRED EMBODIMENTS

Figure 4:
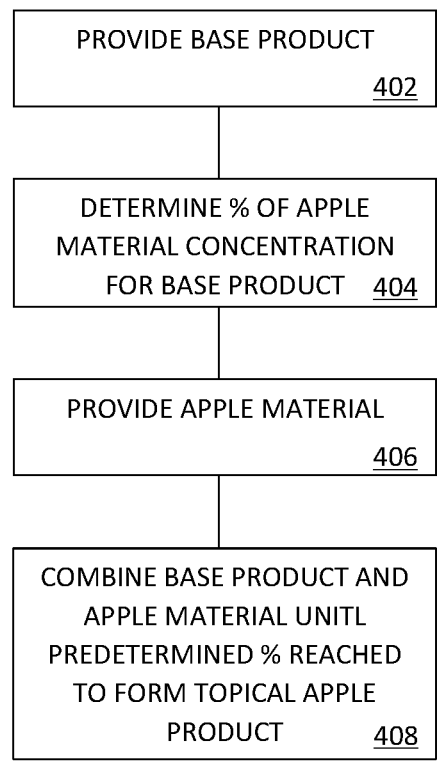
FIG. 4 is a flowchart showing an embodiment of a method of making a topical apple product, in accordance with aspects of the inventive concept.

Various aspects of the inventive concepts will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

In accordance with aspects of the present invention, there are provided various topical apple products comprising apple material, such as apple peel powder, extract or the like. As will be discussed further below, the topical apple products can take any of a variety of forms, including, but not limited to, cosmetic, and non-cosmetic topically applied to the skin, hair, teeth, or other tissue. Various forms of apple material have antioxidant properties that can be particularly advantageous for treating and/or repairing various skin ailments and/or conditions. The topical apple product can take the form of a liquid, lotion, gel, paste, salve, ointment, cream, rub, powder, extract, wax, or spray, as examples, that can be applied to skin, hair, teeth, and/or nails.

As an example, various methods have been used to make apple peel powder from apple skins, such as those described in U.S. Pat. No. 8,551,554 (the '554 Patent"), the contents of which are incorporated herein by reference. The '554 Patent primarily described manners of making such a powder in view of studies showing in vitro cancer fighting benefits. For therapeutic purposes, the '554 Patent described making the apple peel powder to have an unusually high phenolic content, i.e., 3.00%. To the limited extent that uses of such a powder were disclosed in the '554 Patent, they were limited to treating and inhibiting the proliferation of liver cancer cells. The apple peel powder is described as being made for oral consumption as a dietary supplement, in tablet or capsule form, or as a food additive or ingredient.

The Liu '554 Patent describes a method that "involves providing an apple peel, subjecting the apple peel to a phytochemical preservation treatment, drying the treated apple peel, and grinding the dried, treated apple peel to a powder" ('554 Patent at col. 2, ll. 60-63). Additionally, the '554 Patent reports the results of testing different apple varieties and different ways of processing the apple peels. For example, the '554 Patent reports that: "The anthocyanin contents of the freeze-dried peels . . . was much higher than the anthocyanin content of the fresh peels . . . an apparent 14-fold increase in the anthocyanin content of the apple peels after blanching and freeze-drying" ('554 Patent at col. 12, ll. 14-21). It also reports that: "The citric acid and ascorbic acid treatments were not effective in preventing oxidation of the phenolic compounds during oven-drying of the apple peels at 60°C. Heat inactivation by blanching the peels for 10 seconds was much more successful" ('554 Patent at col. 12, ll. 6-64).

Other testing showed that: "The untreated freeze-dried peels had similar phytochemical contents and water activity to the blanched peels. However, the presence of potentially active enzymes in the untreated peels could lead to problems with the apple peel powder during storage and in food applications. Peels blanched for 10 seconds and freeze-dried before being ground to a powder would make the most stable product" ('554 Patent at col. 13, ll. 46-53). "The decreased water activity could allow for greater chemical stability and increased shelf-life of the apple peel powder" ('554 Patent at col. 13, ll. 40-41). Thus: "After reviewing the data, the peels were blanched for 10 seconds and freeze-dried to make the most stable food ingredient, with high phytochemical contents . . . . " ('554 Patent at col. 11, ll. 51-53).

Leahy Orchards Inc. of Canada produces an organic dried apple peel powder under the tradename AppleActiv DAPP™. Some of the significant characteristics of AppleActiv DAPP™ are: high phenolic and flavonoid content, rich in antioxidants, enzymes, vitamins and minerals; and provide clinically supported health benefits. As in the '554 Patent, this product is promoted as a dietary supplement or food ingredient to be consumed and digested by a living being (e.g., person). Other approaches to producing dried apple peel powder may also suffice, so the present invention need not be limited to the methods disclosed in the '554 Patent.

In contrast to uses where apple peel powder (APP) is consumed and digested into the body, the present invention includes novel products and uses of products that include apple material, such as apple peel powder or extract, for application as a topical agent or ingredient in a topical apple product. The apple material can be an apple peel powder made for a method described in the '554 Patent and/or can take the form of AppleActiv DAPP from Leahy Orchards Inc., or the like. In various embodiments, the apple powder and/or apple peel extract is made by extracting phytochemicals from apple peels using a phytochemical treatment process, drying the treated apple peel, and grinding the dried, treated apple peel to a powder.

In a preferred form, the apple material preferably includes Polyphenols/Total Antioxidant Activity of ≥3.00%. But in some embodiments, a topical apple product having apple material having Polyphenols/Total Antioxidant Activity of 0.00%< and <3.00% could also provide treatment, repair, and/or prevention improvements and advantages over the base topical product without the apple material, e.g., a topical apple product having Polyphenols/Total Antioxidant Activity of 0.00%< and ≤0.50%, 0.50%< and ≤1.00%, 1.00%< and ≤1.50%, 1.50%< and ≤2.00%, 2.00%< and ≤2.50%, and/or 2.50%< and ≤3.00% could be advantageously provided. In some embodiments, the Polyphenols/Total Antioxidant Activity of can be between in a range of about 3% to about 10%, 10% to 20%, and/or 20% to about 35%, or more.

The topical apple product can be formed by adding the apple peel material to a "base product" or "base topical product." The base product can take the form of a liquid, lotion, gel, paste, salve, ointment, cream, rub, powder, extract, wax, or spray, as examples. The base product could be a product suitable for application to skin, hair, teeth, and/or nails.

Figures 1, 2, 3:
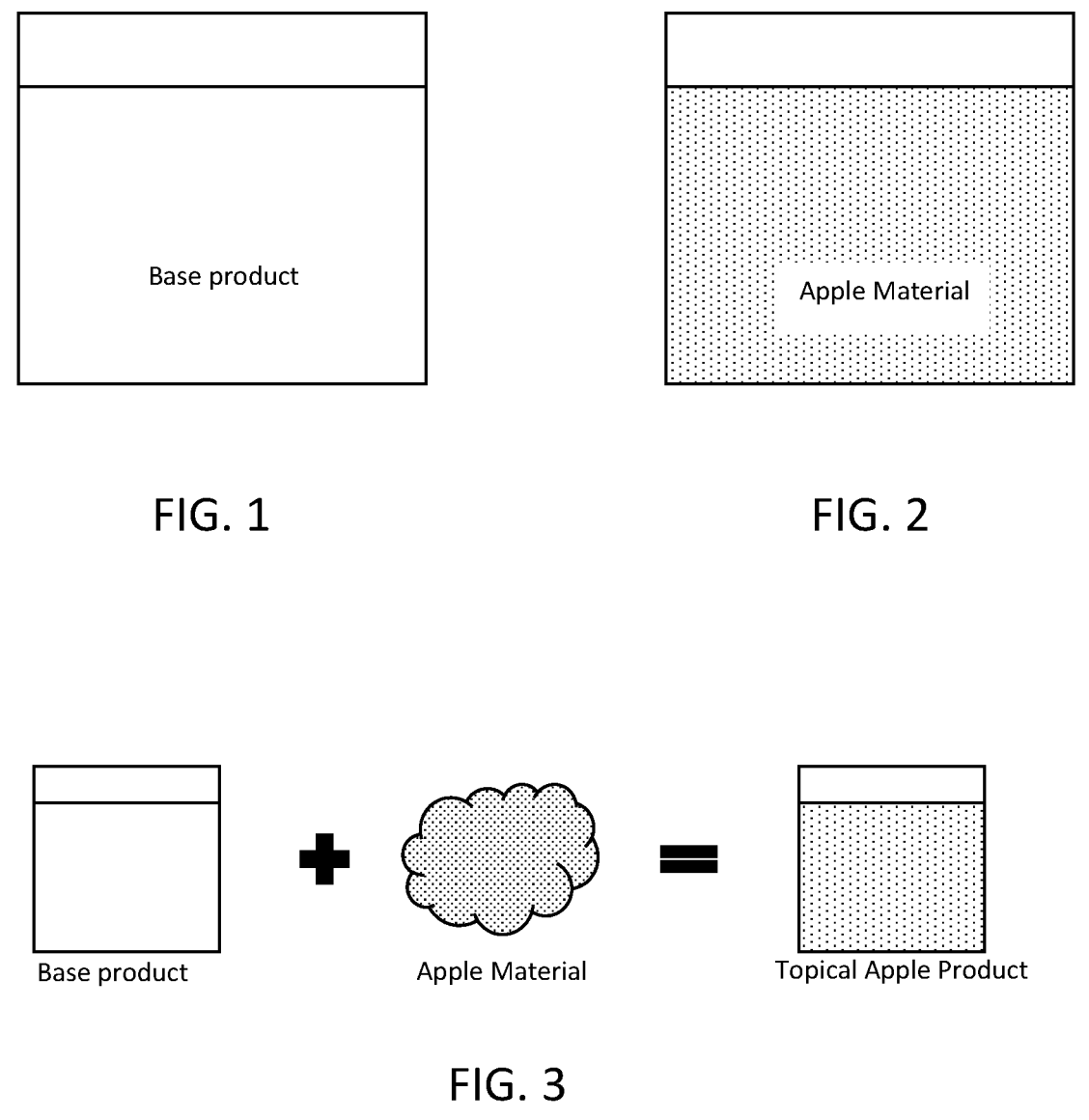

FIG. 1 shows an embodiment of a container holding a base topical product and FIG. 2 shows an embodiment of a container holding an apple material. The precise amount of apple material, e.g., dried apple peel powder or liquid extract added to a base topical product will vary depending on the intended use of the product. For example, when used in a cosmetic product, such as makeup, the apple material can be generally undetectable from the look, feel, consistency, and application perspectives of the base topical product. That is, in various embodiment the topical apple product can appear to the consumer and user to be no different, or not substantially different, than the base topical product without the apple material. The apple material need not alter, or substantially alter, the look, feel, consistency, and/or application of the base topical product, while providing significant repair and/or treatment benefits to the area of application (e.g., damaged skin).

As examples, the topical apple product can take the form of any of the following (base product+apple material (e.g., Dried apple peel powder, liquid apple extract, or the like): face and/or body lotion, such as moisturizers and cleansers, skin serums, body powder, sunscreen, bronzer, shampoo, conditioner, soap, hair color, hair detangler, mask, peel, lipstick, lip gloss, lip balm, foundation, blush, toner, mascara, eye shadow, eye and anti-aging solutions, shave cream, lotion, or gel, aftershave, deodorant, antiperspirant, cologne, perfume, body splash, toothpaste, floss, and/or mouthwash or mouth rinse. As other examples, the topical apple product can be a medical treatment product, such as a first aid cream or spray or other skin treatment cream or spray, such as for use to treat a wound, skin irritation, burn, rash, eczema, infection, and/or melanoma, or the like.

FIG. 3 shows a notional example of a base product and apple material being combined to form a topical apple product.

Depending on the particular base product, different techniques can be used to combine in the apple material with the base product. Preferably, in most embodiments, the selected technique achieves equal, or substantially equal, suspension and a uniform consistency in the base products, e.g., liquids, gels, or solids (e.g., lipstick, deodorant, etc.). That is, preferably, the addition of the apple material does not adversely alter the consistency of the base product. For example, the apple material, e.g., dried apple peel powder, liquid extract, or the like, can be combined (e.g., mixed) into a complete base product, such as a lotion, powder, gel, or the like, as shown in the representative method 400 of FIG. 4. Or, in other embodiments, the apple material, e.g., dried apple peel powder, liquid extract, or the like, can be combined (e.g., mixed) with base product constituents, during the process of making the base product to form a topical apple product.

In the method 400 of FIG. 4, a base topical product is provided in step 402. A percentage of applicant material within the final topical apple product is determined. The apple material is provided to achieve the determined percentage. And the base topical product and the apple material are combined to form the topical apple product having the predetermined amount of apple material.

Figure 5:
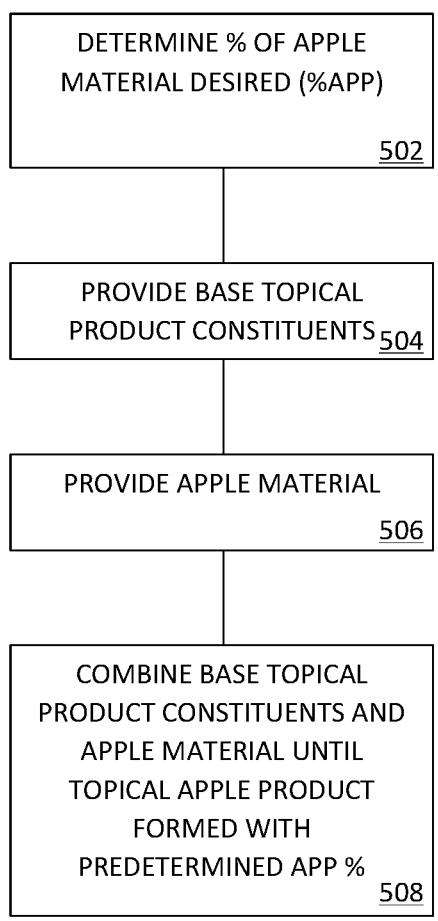
FIG. 5 is a flowchart showing an embodiment of another method of making a topical apple product, in accordance with aspects of the inventive concept.

FIG. 5 shows another method 500 of making the topical apple product. In this method the apple material is added while making the base topical product, to collectively form the topical apple product. In step 502, a percentage of apple material is determined for a total amount of topical apple product or determined amount of base topical product. The base topical product constituents are provided and the apple material is provided as an additional constituents. The constituents are combined and processed to form a topical base product having the predetermined percentage of apple material, e.g., dried apple peel powder and/or liquid apple extract.

In various embodiments of methods used in making a topical apple product, an appropriate amount of apple material, e.g., as a percentage of the base product, can be predetermined, such as by a machine capable of volume and/or weight measures. This percentage can be variously determined based on several factors, such as not exceeding an amount (apple material threshold amount) that would adversely affect the look, feel, texture, consistency, odor, and/or performance of the base product, such as for cosmetics and other product that are not primarily palliative. For medical topical base products, some or all of these factors may be less of a consideration. For example, in various embodiments, a topical apple product may include a percentage of apple material that is greater than 0% and up to about 50%, while in other embodiments, the percentage may be greater than 0% and up to about 25%, while in still other embodiments, the percentage may be greater than 0% and up to about 10%, while still in other embodiments, the percentage may be greater than 0% and up to about 5%. Depending on the embodiment, the percentage of apple material in a topical apple product could be of still another percentage. In the methods of FIGS. 4 and 5, as examples, the amount of apple material to be added to the base product is predetermined. This can be done by an automated machine configured to determine the appropriate quantities of apple material and/or base topical material to form the topical apple product having the predetermined and desired amount of apple material.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

It is appreciated that certain features of the invention, which are, for clarity, described in the context of separate embodiments, may also be provide in combination in a single embodiment. Conversely, various features of the invention which are, for brevity, described in the context of a single embodiment may also be provided separately or in any suitable sub-combination.

For example, it will be appreciated that all of the features set out in any of the claims (whether independent or dependent) can be combined in any given way.

What is claimed is:

1. A method of making a topical apple product consisting essentially of a non-food base topical material and a processed apple material, the method comprising:
   selecting the base topical material from the group consisting of a lotion, a paste, a gel, a cream, a non-aqueous liquid, and a powder having cosmetic and/or therapeutic applications when topically applied to human skin, hair, teeth and/or nails;
   preparing the processed apple material by sequentially blanching and freeze-drying apple peels to preserve and stabilize phytochemicals in the apple peels to form dried processed apple peel powder and/or processed apple peel extract that has a shelf-stable Polyphenols/Total Antioxidant Activity of ≥3.00%; and
   combining a predetermined amount of the processed apple material with an amount of the base topical material until the two are substantially uniformly combined to form the topical apple product containing greater than 0% up to about 50% of the processed apple material and having substantially equal and a uniform consistency.

2. The topical apple productmethod of claim 1, wherein the processed apple material comprises processed apple peel extract.

3. The method of claim 1, wherein the processed apple material comprises dried processed apple peel powder.

4. The method of claim 1, wherein the processed apple material further includes some apple flesh.

5. The method of claim 1, wherein the processed apple material comprises antioxidants.

6. The method of claim 1, wherein the dried processed apple peel powder and/or processed apple peel extract comprises Polyphenols/Total Antioxidant Activity in a range of about 20% to about 35%.

7. The method of claim 1, wherein the base topical material is a cosmetic product.

8. The method of claim 1, wherein the base topical material is selected from the group consisting of:
   face lotion, facial moisturizers, facial cleansers, body lotion, body moisturizer, body cleanser, skin serums, body powder, sunscreen, bronzer, shampoo, conditioner, soap, hair color, hair detangler, mask, peel, lipstick, lip gloss, lip balm, foundation, blush, toner, mascara, eye shadow, anti-aging solutions, shave cream, lotion, gel, aftershave, deodorant, antiperspirant, cologne, perfume, body splash, toothpaste, mouthwash, and mouth rinse.

9. The method of claim 1, wherein the base topical material is selected from the group consisting of:
   a topical medical treatment product, a first aid cream and spray, a skin treatment cream and spray for use to treat a wound, skin irritation, burn, rash, eczema, infection, and/or melanoma.

10. The method of claim 1, wherein the percentage of dried processed apple peel powder and/or processed apple peel extract in the topical apple product is sufficient to provide significant repair, prevention and/or treatment benefits to an area of application.

11. The method of claim 1, wherein the percentage of dried processed apple peel powder and/or processed apple peel extract in the topical apple product is greater than 0% and up to about 25% of the topical apple product.

12. The method of claim 1, wherein the percentage of dried processed apple peel powder and/or processed apple peel extract in the topical apple product is greater than 0% and up to about 10% of the topical apple product.

13. A method of making a topical apple product consisting essentially of a non-food base topical material and a processed apple material, the method comprising:
   selecting the base topical material from the group consisting of a lotion, a paste, a gel, a cream, a non-aqueous liquid, and a powder having cosmetic and/or therapeutic applications when topically applied to human skin, hair, teeth and/or nails;
   preparing the processed apple material by sequentially blanching and freeze-drying apple peels to preserve and stabilize phytochemicals in the apple peels to form dried processed apple peel powder and/or processed apple peel extract that has a shelf-stable Polyphenols/Total Antioxidant Activity of ≥3.00%; and
   combining a predetermined amount of the processed apple material with an amount of the base topical material until the two are substantially uniformly combined to form the topical apple product containing greater than 0% up to about 50% of the processed apple material and having substantially equal and a uniform consistency,
   wherein the base topical material is selected from the group consisting of:
      face lotion, facial moisturizers, facial cleansers, body lotion, body moisturizer, body cleanser, skin serums, body powder, sunscreen, bronzer, shampoo, conditioner, soap, hair color, hair detangler, mask, peel, lipstick, lip gloss, lip balm, foundation, blush, toner, mascara, eye shadow, anti-aging solutions, shave cream, lotion, gel, aftershave, deodorant, antiperspirant, cologne, perfume, body splash, toothpaste, mouthwash, and mouth rinse.

14. The method of claim 13, wherein the processed apple material comprises antioxidants.

15. The method of claim 14, wherein the processed apple material comprises processed apple peel extract and/or dried processed apple peel powder.

16. The method of claim 13, wherein the processed apple material further includes some apple flesh.

17. A method of making a topical apple product consisting essentially of a non-food base topical material and a processed apple material, the method comprising:
   selecting the base topical material from the group consisting of a lotion, a paste, a gel, a cream, a non-aqueous liquid, and a powder having cosmetic and/or therapeutic applications when topically applied to human skin, hair, teeth and/or nails;
   preparing the processed apple material by sequentially blanching and freeze-drying apple peels to preserve and stabilize phytochemicals in the apple peels to form dried processed apple peel powder and/or processed apple peel extract that has a shelf-stable Polyphenols/Total Antioxidant Activity of ≥3.00%; and
   combining a predetermined amount of the processed apple material with an amount of the base topical material until the two are substantially uniformly combined to form the topical apple product containing greater than 0% up to about 50% of the processed apple material and having substantially equal and a uniform consistency, wherein the base topical material is selected from the group consisting of:

a topical medical treatment product, a first aid cream and spray, a skin treatment cream or spray for use to treat a wound, skin irritation, burn, rash, eczema, infection, and/or melanoma.

18. The method of claim 17, wherein the processed apple material comprises antioxidants.

19. The method of claim 18, wherein the processed apple material comprises processed apple peel extract and/or dried processed apple peel powder.

20. The method of claim 19, wherein the dried processed apple peel powder and/or processed apple peel extract comprises Polyphenols/Total Antioxidant Activity in a range of about 20% to about 35%.

21. The method of claim 15, wherein the dried processed apple peel powder and/or processed apple peel extract comprises Polyphenols/Total Antioxidant Activity in a range of about 20% to about 35%.

\* \* \* \* \*

UNITED STATES PATENT AND TRADEMARK OFFICE
CERTIFICATE OF CORRECTION

PATENT NO. : 12,414,912 B2  
APPLICATION NO. : 17/741999  
DATED : September 16, 2025  
INVENTOR(S) : Ross Anapolle Page 1 of 1

It is certified that error appears in the above-identified patent and that said Letters Patent is hereby corrected as shown below:

In the Claims

At Column 7, Line 33:
"The topical apple productmethod of claim 1"
Should read:
--The method of claim 1--

Signed and Sealed this  
Twenty-seventh Day of January, 2026

John A. Squires  
*Director of the United States Patent and Trademark Office*